(12) United States Patent
De Zeeuw et al.

(10) Patent No.: US 8,506,688 B2
(45) Date of Patent: Aug. 13, 2013

(54) GAS CHROMATOGRAPHIC DEVICE

(75) Inventors: Jaap De Zeeuw, Middleburg (NL); Jack Cochran, State College, PA (US); Scott L. Grossman, Bellefonte, PA (US)

(73) Assignee: Restek Corporation, Bellefonte, PA (US)

( * ) Notice: Subject to any disclaimer, the term of this patent is extended or adjusted under 35 U.S.C. 154(b) by 322 days.

(21) Appl. No.: 12/009,420

(22) Filed: Jan. 18, 2008

(65) Prior Publication Data

US 2009/0183634 A1 Jul. 23, 2009

(51) Int. Cl.
 *B01D 53/02* (2006.01)
 *G01N 30/02* (2006.01)
 *G01N 30/60* (2006.01)

(52) U.S. Cl.
 USPC ............... 96/106; 96/101; 96/104; 96/105; 73/23.35; 73/23.39; 73/23.42

(58) Field of Classification Search
 USPC ...... 96/101, 104, 105, 106; 95/89; 73/23.35, 73/23.39, 23.41, 23.42
 See application file for complete search history.

(56) References Cited

U.S. PATENT DOCUMENTS

| | | | | |
|---|---|---|---|---|
| 4,383,839 A | * | 5/1983 | Sisti et al. | 95/83 |
| 4,405,344 A | * | 9/1983 | Sisti et al. | 95/89 |
| 4,526,686 A | * | 7/1985 | Sisti et al. | 210/198.2 |
| 5,252,109 A | * | 10/1993 | Munari et al. | 95/87 |
| 5,611,846 A | * | 3/1997 | Overton et al. | 96/102 |
| 5,714,677 A | * | 2/1998 | Parsy et al. | 73/23.41 |
| 5,954,862 A | * | 9/1999 | Wilson | 96/101 |
| 6,203,597 B1 | * | 3/2001 | Sasano et al. | 95/87 |
| 6,301,952 B1 | | 10/2001 | De Zeeuw et al. | |
| 6,494,939 B1 | * | 12/2002 | Tipler | 96/105 |
| 6,652,625 B1 | * | 11/2003 | Tipler et al. | 95/82 |
| 6,969,095 B2 | | 11/2005 | Rittenhouse | |
| 6,974,495 B2 | * | 12/2005 | Tipler et al. | 96/105 |
| 2006/0113231 A1 | * | 6/2006 | Malik | 210/198.2 |
| 2006/0286677 A1 | | 12/2006 | Wohleb et al. | |

OTHER PUBLICATIONS

De Zeeuw, J. et al., "A Simple Way to Speed up Separations by GC-MS Using Short 0.53 mm Columns and Vacuum Outlet Conditions," J. High Resol. Chromatogr., Dec. 2000, pp. 677-680.

Peene, J. et al., "Low Pressure Case Chromatography: Fast Analysis With High Sensitivity," International Laboratory, Sep. 2000, pp. 41-44.

Restek catalog excerpts found on restek.com. "Splitless Liners for Agilent: 4 mm Splitless," retrieved on Jan. 14, 2008.

Restek catalog excerpts found on restek.com. "Press Tight Connectors: Deactivated, Universal," retrieved on Jan. 14, 2008.

Stevenson, Robert, "Editor's Page, The World of Separation Science: The Smarter The Chromatographer, The Shorter The Columns." American Laboratory, Feb. 2000, pp. 6-10.

(Continued)

*Primary Examiner* — Robert Clemente

(57) ABSTRACT

A gas chromatographic device comprises an inlet system and a chromatography column. The inlet system includes a liner having pressure reducing means contained therein for reducing pressure between an inlet of the pressure reducing means and an outlet of the pressure reducing means. When the devise is in use, the chromatography column is positioned in the liner of the inlet system downstream from the pressure reducing means, and the chromatography column is under vacuum at its outlet.

22 Claims, 3 Drawing Sheets

(56) References Cited

OTHER PUBLICATIONS

Stevenson, Robert, "Editor's Page, The World of Separation Science: 22nd International Symposium on Capillary Chromatography." American Laboratory, Feb. 2000, pp. 6-10.

Varian Analytical Instruments' brochure, entitled, "Varian Rapid—MS System," undated.

Press Release by Varian, Inc., entitled, "Rapid-MS from Varian, Inc. Boosts GC/MS Productivity up to 10 Fold," undated.

Excerpts from EPA Method 529 (Rev. 1.0), "Illustrating GC-MS Analysis of Explosives without Flow Restriction," undated, www.epa.gov/nerlcwww/m_529.pdf.

International Search Report issued by the International Searching Authority in PCT International Application No. PCT/US09/00323, completed on Mar. 8, 2009.

Written Opinion of the International Searching Authority issued by the International Searching Authority in PCT International Application No. PCT/US09/00323, completed on Mar. 8, 2009.

* cited by examiner

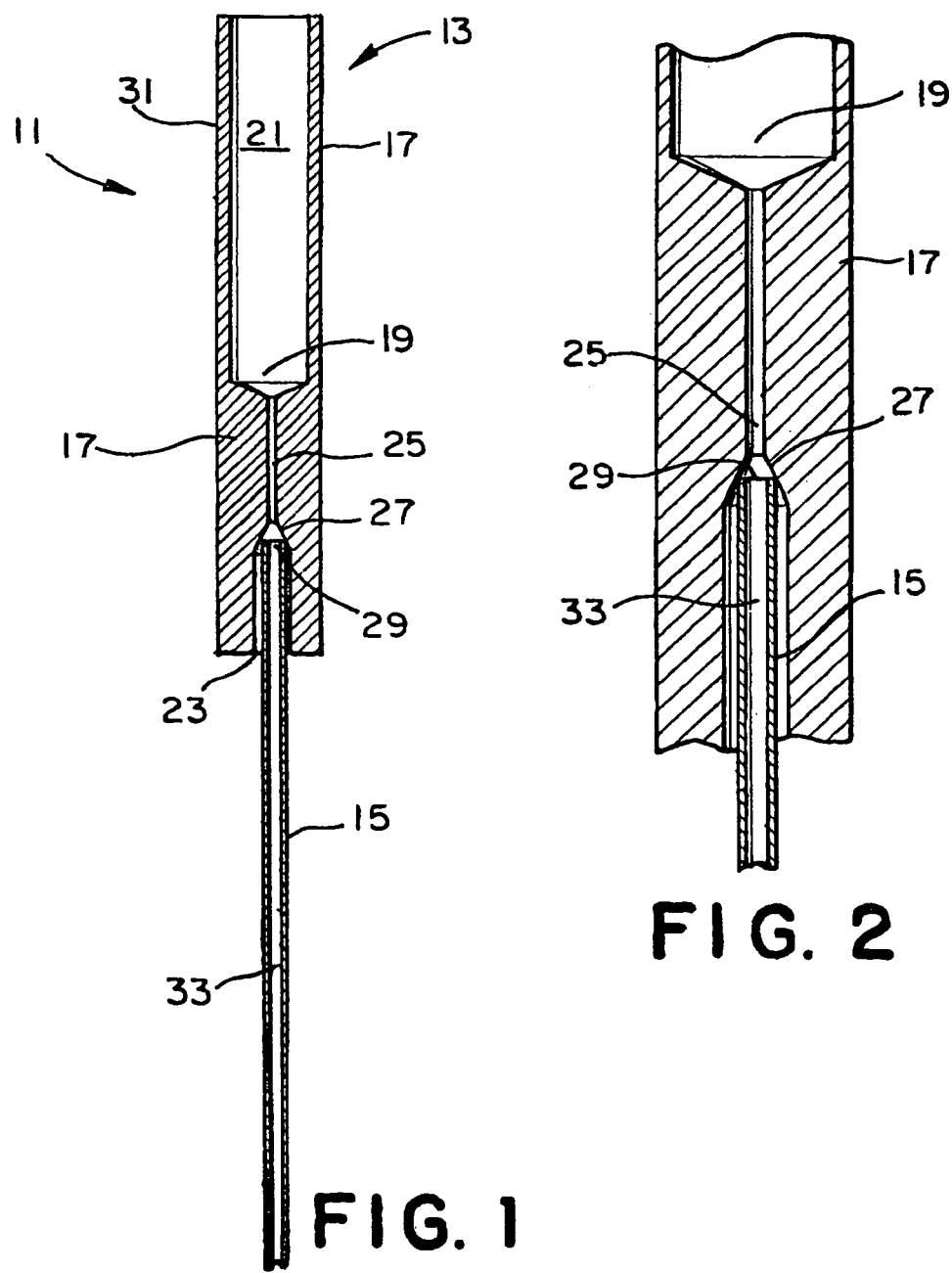

GAS CHROMATOGRAPHIC DEVICE

FIELD OF THE INVENTION

This invention relates to gas chromatography, and more particularly concerns new gas chromatographic devices having pressure reducing means contained in a liner of the inlet system of such devices for reducing pressure such that the chromatography column of such devices operates under vacuum at its outlet.

BACKGROUND OF THE INVENTION

De Zeeuw et al. U.S. Pat. No. 6,301,952, issued on Oct. 16, 2001, for a Gas Chromatographic Device, disclosed that prior to their invention, chromatography columns in GC/MS systems were often very long to provide the necessary pressure drop between the inlet, where the inlet pressure of the chromatography column was above atmospheric, to the outlet of the chromatography column, where the outlet pressure of the chromatography column was essentially vacuum because the chromatography column ended in the ionization chamber of the mass spectrometer, thereby resulting in long periods of time needed to perform the sample analyses. De Zeeuw et al. U.S. Pat. No. 6,301,952, in its background section, indicated that although smaller bore columns having a reduced length could be used to provide the pressure drop, such columns had disadvantages of a limited sample capacity, installation and operation problems, and a problem regarding eluted peaks being too fast to record using mass spectrometry systems.

De Zeeuw et al. U.S. Pat. No. 6,301,952, which is incorporated herein by reference, discloses a gas chromatographic device comprising an inlet system, a chromatography column, and a pressure reducing means disposed therebetween for reducing pressure between an inlet of the pressure reducing means and the outlet of the chromatography column. In an alternative embodiment disclosed in the De Zeeuw et al. U.S. Pat. No. 6,301,952, a gas chromatographic device comprises an inlet, a wide-bore column having an inlet and an outlet, and a pressure reducing means being coupled to the outlet of the column for providing a vacuum condition at the outlet of such pressure reducing means. The pressure reducing means disclosed in the De Zeeuw et al. U.S. Pat. No. 6,301,952 is a coiled tubular shaped restrictor column which is integrally attached with connectors (either permanently or using ferrules or press-fit connectors) to the chromatography column. The restrictor column is susceptible to contamination at its inlet, thereby requiring repeated clipping off of a short length of the restrictor column at its inlet to clear the sample path. In the event that the restrictor column becomes too short due to repeated clipping, the restrictor column must be replaced requiring mechanically removing the connector (e.g., a ferrule-based connector) or clipping off the permanent connector or press-fit connector in order to connect a new restrictor column to the chromatography column using either a new permanent connection or a new ferrule-based connection or new press-fit connection. With each restriction column trimming, the flow path is shortened, resulting in potential run-to-run variance. With the ferrule-based connectors, the replacement process is labor intensive and requires prolonged opening of the GC oven. Further, since the restrictor column resides in the GC oven, it is therefore subject to the same temperature ramp of the analysis. Accordingly, this results in a complex gas flow profile that may be difficult to reproduce over repeated runs where the length of the restrictor column changes each time it is clipped by the above-mentioned trimming process.

SUMMARY OF THE INVENTION

An object of our invention is to overcome the disadvantages of the invention of De Zeeuw et al. U.S. Pat. No. 6,301, 952, while retaining the advantages thereof. These advantages include using chromatography columns that are relatively reduced in length when compared with the prior art before De Zeeuw et al. U.S. Pat. No. 6,301,952, which enables short analysis times of samples. Still another of these advantages is eluted peaks in accordance with our invention have sufficient peak width (in seconds) to be properly integrated by contemporary mass spectrometry systems. Another of these advantages is that under vacuum the optimal linear gas velocity increases about tenfold and that components elute from the chromatography column at lower temperatures which is especially important for thermolabile and high boiling components. Yet another advantage is the reduced chromatography column bleeding, resulting in the chromatography column having a life-time that is generally longer than that of chromatography columns prior to the invention of De Zeeuw et al. U.S. Pat. No. 6,301,952. Additional advantages include: eliminating the need to couple the chromatography column via a restriction to the ionization chamber of the mass spectrometer so that no leaks occur; a fixed or standard inlet pressure may be used which is preferably 10 kPa to 1000 kPa, and more preferably 10 kPa to 250 kPa; and the pressure prevailing at the outlet of the pressure reducing means is 0.00001 kPa to 50 kPa (absolute pressure), preferably 0.01 kPa to 20 kPa (absolute pressure).

These and/or other objects, such as providing a pressure reducing means having a fixed diameter within the confines of the GC inlet and/or providing means for removably attaching the chromatography column to the pressure reducing means without the need of tools or the need to clip off the pressure reducing means, are accomplished by our invention which is disclosed below.

BRIEF DESCRIPTION OF THE DRAWINGS

FIG. 1 is a schematic view of a gas chromatographic device constructed in accordance with our invention;

FIG. 2 is an enlarged view of a portion of the schematic view shown in FIG. 1;

DETAILED DESCRIPTION

Figure 3:
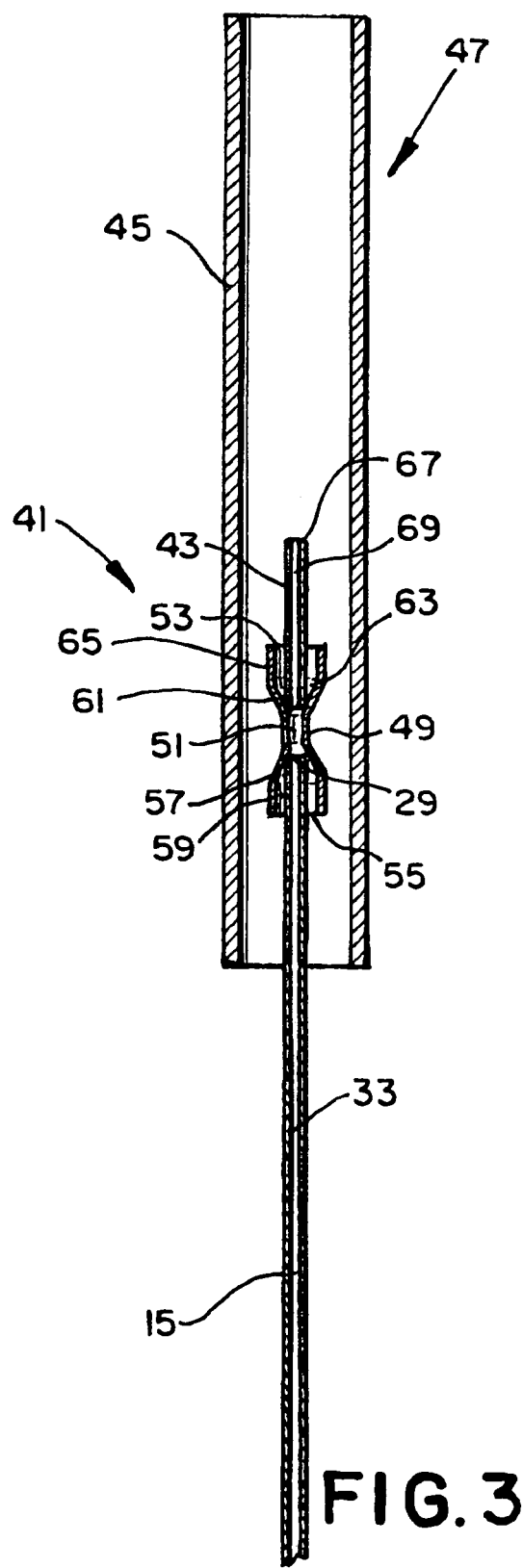
FIG. 3 is a schematic view of an alternative embodiment of the invention.

Turning now to the drawings, there is shown in FIGS. 1 and 2 a gas chromatographic device 11 constructed in accordance with our invention, which includes an inlet system 13 and a chromatography column 15.

In this embodiment of the invention, the inlet system 13 includes a liner 17 having a pressure reducing means contained therein for reducing pressure between the inlet of the pressure reducing means and the outlet of the pressure reducing means. Specifically, in this embodiment of the invention, the liner 17 has a passageway 19 extending therethrough between its inlet 21 and its outlet 23, and the passageway 19 has a pressure reducing portion 25 sufficient to reduce the pressure of gas entering the passageway 19 through the inlet 21. Preferably, the pressure reducing portion 25 of passageway 19 has a circular cross section having a diameter in a range between 0.1 mm and 5.0 mm.

The liner 17 has a surface 27 along the passageway 19 downstream of the pressure reducing portion 25 of the passageway 19 which when the device 11 is in use contacts the inlet portion 29 of the chromatography column 15. Preferably, the surface 27 has a frusto-conical shape that abuts against the inlet portion 29 of the chromatography column 15 when the liner 17 rests on the inlet portion 29 of the chromatography column 15 for facilitating mating contact between the liner 17 and the inlet portion 29 of the chromatography column 15 to create a gastight seal therebetween. Because the liner 17 is stacked vertically (directly above and in contact with) the inlet portion 29 of the chromatography column 15 when the device 11 is in use, a gastight seal is obtained between the frusto-conical shaped surface 27 and the inlet portion 29 of the chromatography column 15 without the need of any additional means for sealing therebetween such as sealants or the like. Accordingly, this structure permits the liner 15, if it should become contaminated, to be easily removed and replaced without the need of tools to disconnect the liner 15 from the inlet portion 29 of the chromatography column 15. Further, the need to repeatedly clip off a portion of a restrictor column, eventually followed by the need to remove an existing permanent connection, mechanical connection, or press-fit connection connecting the restrictor column to the chromatography column and to make a new permanent connection, a new mechanical connection, or a new press-fit connection linking the chromatography column 15 to a new restrictor column, as was required in accordance with one of the embodiments disclosed in De Zeeuw U.S. Pat. No. 6,301,952, does not exit with our invention. A liner 17, in accordance with our invention, may be removably attached to the chromatography column 15 by merely stacking the liner 17 on the inlet portion 29 of the chromatography column 15 so that the surface 27 of the liner 17 rests on the inlet portion 29 of the chromatography column 15. If a liner 17 becomes contaminated, it may be easily replaced by unstacking it from on top of the inlet portion 29 of the chromatography column 15 without having to use tools to disconnect or remove a connector since there is no connector, followed by merely stacking a new liner 17 onto the inlet portion 29 of the chromatography column 15 so that the surface 27 of the new liner rests on the inlet portion 29 of the chromatography column 15.

The dimensions of the liner 17 are dependent upon the desired pressure drop/gas flow rate through the device. Preferably, the length of the liner 17 is about 8 cm. The pressure reducing portion 25 of the passageway 19 preferably has a length of about 0.1 cm to about 2 cm. Preferably, the pressure reducing portion 25 of the liner 17 has a diameter of 0.0001 mm to 5.0 mm, and a diameter between 0.030 mm and 0.015 mm is more preferred. The liner 17 is preferably made from an inert, substantially non-absorbing material such as glass, fused silica, quartz, chemically inert metal, an inert material, or materials coated with an inert material. The passageway 19 extending therethrough may be formed using laser drilling. Alternatively, liner 17 may be formed using glass drawing technology used to make capillary tubes and columns. Also, the passageway 19 of liner 17 may be formed by creating the pressure reducing portion 25 of the passageway 19 with a capillary tube and forming the remainder of the liner 17 around the capillary tube using, for example, heat fusing technology, to hold the capillary tube in place. The liner may also have a hole in top or bottom.

The chromatography column 15 preferably is made of silica, glass, metal, an organic polymer, an inorganic polymer, or a combination thereof. The chromatography column 15 preferably has a length in a range between 0.25 m to 100 m, and more preferably in a range between 0.5 m to 25 m. An average internal diameter of the chromatography column 15 preferably is in a range between 0.05 mm to 1.0 mm, and more preferably in a range between 0.25 mm to 0.75 mm, and an average outer diameter of the chromatography column 15 preferably is in a range between 0.2 mm to 1.0 mm, and more preferably in a range between 0.4 mm to 0.8 mm. The internal surface of the chromatography column 15 may be deactivated with a chemical and/or physical deactivation agent. Examples of suitable deactivation agents are octamethyl tetrasiloxane, hydrosilane or of the polyethylene glycol type. The internal surface of these columns may additionally be coated, not only with bonded and/or cross linked liquid or solid stationary phases, but also with non-bonded and/or non-crosslinked stationary phases having an average film thickness of 0.05 μm to 100 μm. Columns with a bonded liquid phase have preferably a film thickness of 0.05 μm to 1.0 μm. If the columns are coated with a solid stationary phase, the average film thickness thereof preferably is 1 μm to 100 μm, and more preferably 2 μm to 50 μm.

In use, the inlet portion 29 of the chromatography column 15 is placed within the inlet system 13 of the gas chromatographic device 11 such that the frusto-conical shaped surface 27 of the liner 17 sits on the inlet portion 29 of the chromatography column 15 creating a gastight seal therebetween. Gas carrying the sample to be tested may be introduced to the liner 17 in its upper end portion 31, and then passed through the pressure reducing portion 25, where the pressure of the gas is reduced, and into and through the chromatography column 15, where the gas exits the chromatography column 15 at the outlet portion of the chromatography column 15 under vacuum conditions.

Figure 4:
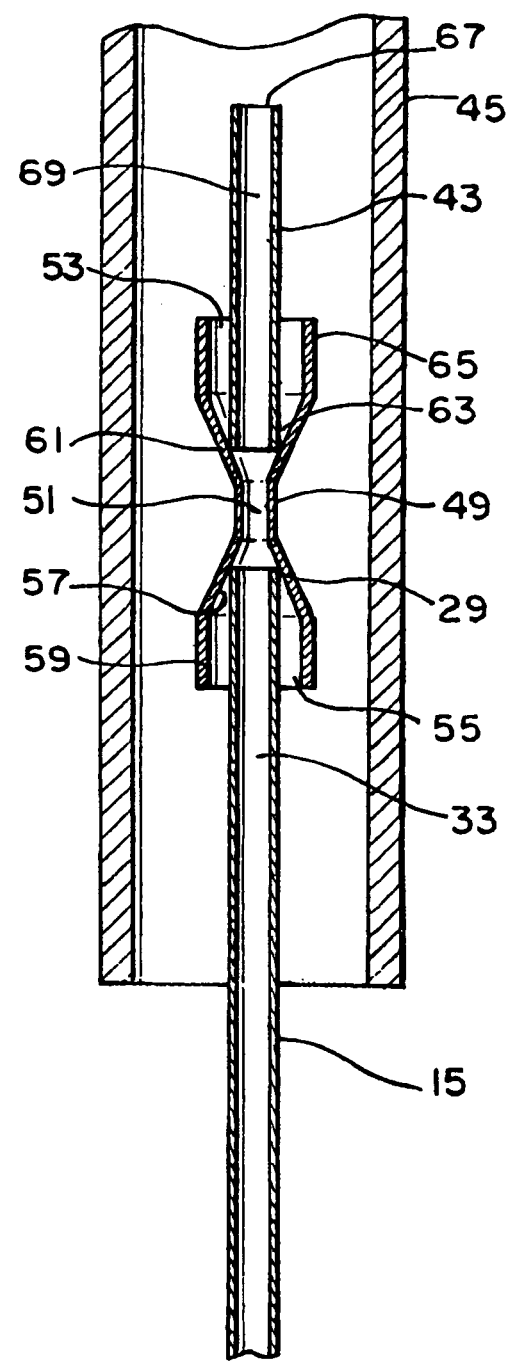
FIG. 4 is an enlarged view of a portion of the schematic view shown in FIG. 3.

Turning now to FIGS. 3 and 4, there is shown an alternative embodiment of our invention, comprising a chromatographic device 41 in which the pressure reducing means comprises a capillary tube 43 contained within a liner 45 of an inlet system 47 of the gas chromatographic device 41.

A column union 49 is provided for coupling the capillary tube 43 to a chromatography column 15. The column union 49, which has a tube-like body, is provided with a passageway 51 extending therethrough between an inlet 53 to the passageway 51 and an outlet 55 from the passageway 51.

The column union 49 is provided with an upright frusto-conical shaped surface 57 along the passageway 51 of the column union 49 for contacting the intlet portion 29 of the chromatography column 15 and creating a gastight seal therebetween. The column union 49 rests on the outlet portion 29 of the chromatography column 15, with the surface 57 of the column union 49 engaging the inlet portion 29 of the chromatography column 15 and the skirt 59 of the column union 49 surrounding the end portion of the chromatography column 15 sufficiently to permit vertical stacking of the column union 49 onto the end portion of the chromatography column 15 to prevent the column union 49 from falling off the end portion of the chromatography column 15. The column union 49 also has an inverted frusto-conical shaped surface 61 along the passageway 51 of the column union 49 for contacting the outlet portion 63 of the capillary tube 43 and creating a gastight seal therebetween. The capillary tube 43 rests on the column union 49, with the outlet portion 63 of the capillary tube 43 engaging the surface 61 of the column union 49 and the skirt 65 of the column union 49 surrounding the end portion of the capillary tube 43 sufficiently to permit vertical stacking of the capillary tube 43 onto the column union 49 to prevent the capillary tube 43 from falling off the column union 49.

Preferably, the capillary tube 43 has a length of about 0.1 cm to about 8 cm, and more preferably of about 0.4 cm to about 2 cm. The capillary tube 43 preferably is made from an inert, substantially non-absorbing material such as glass, fused silica, quartz, chemically inert metal, inert materials, or materials deactivated with an inert material, and is manufactured using conventional methods.

Preferably, the capillary tube 43 has an average internal diameter of 0.005 mm to 0.1 mm, and more preferably an average internal diameter of 0.0150 mm to 0.030 mm.

Alternatively, the capillary tube 43 has an average internal diameter of 0.1 mm to 5.0 mm, and more preferably an average internal diameter of 0.2 mm to 2.0 mm, and preferably is packed with deactivated or non-deactivated particles having an average size of 0.5 μm to 500 μm (micrometer) (more preferably 5 μm).

The column union 49 preferably has a length of about 2 cm. The column union 49 preferably is made from glass, quartz or silica using conventional methods, and is deactivated.

In this embodiment of the invention, the liner 45 is a conventional liner.

In use, the inlet portion 29 of the chromatography column 15 is placed within the liner 45 of the inlet system 47 of the gas chromatographic device 41. The column union 49 is removably attached to the chromatography column 15 by being stacked vertically onto the inlet portion 29 of the chromatography column 15 such that the surface 57 of the column union 49 rests on the inlet portion 29 of the chromatography column 15 and the skirt 59 of the union column 49 surrounds the end portion of the chromatography column 15. The capillary tube 43 is removably attached to the column union 49 by being stacked vertically onto the column union 49 such that the outlet portion 63 of the capillary tube 43 rests on the surface 61 of the union column 49 and the skirt 65 of the union column 49 surrounds the end portion of the capillary tube 43 at its outlet portion 63. Gas carrying the sample to be tested may be introduced into the liner 45, then passed into the inlet portion 67 of the capillary tube 43 and through the passageway 69 of the capillary tube 43 resulting in reducing the pressure of the gas, then through the passageway 51 of the column union 49 into and through the passageway 33 extending through the chromatography column 15, where the gas exits the chromatography column 15 at the outlet portion of the chromatography column under vacuum conditions.

Generally, if the capillary tube 43 becomes contaminated, it may be easily replaced by pulling it from the column union 49 and placing a new capillary tube 43 into the column union 49 or by removing both the column union 49 and the contaminated capillary tube 43 by pulling the column union 49 off the inlet portion 29 of the chromatography column 15 and placing a new column union 49 onto the end portion of the chromatography column 15 and placing a new capillary tube 43 into the column union 49. Again, no tools or clipping are required to disconnect the components being replaced. However, if the temperature at the column unison 49 during operation of the device 41 rises above about 200° C., the column union 49 may stick to the capillary tube 43 and/or the chromatography column 15, requiring clipping to replace a contaminated capillary tube 43.

Figure 5:
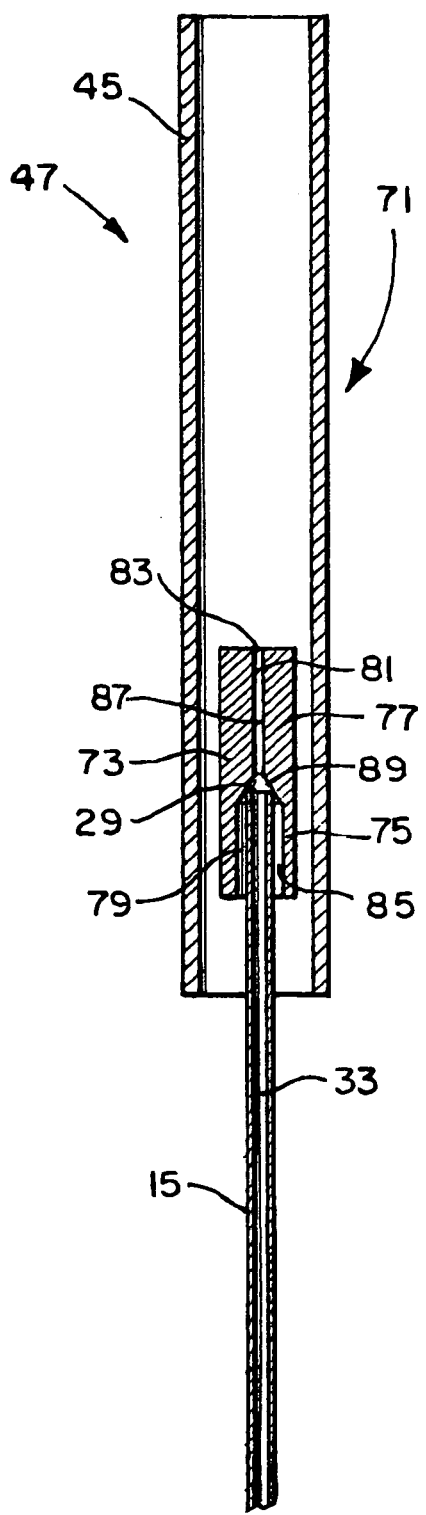
FIG. 5 is a schematic view of another embodiment of the invention.
Figure 6:
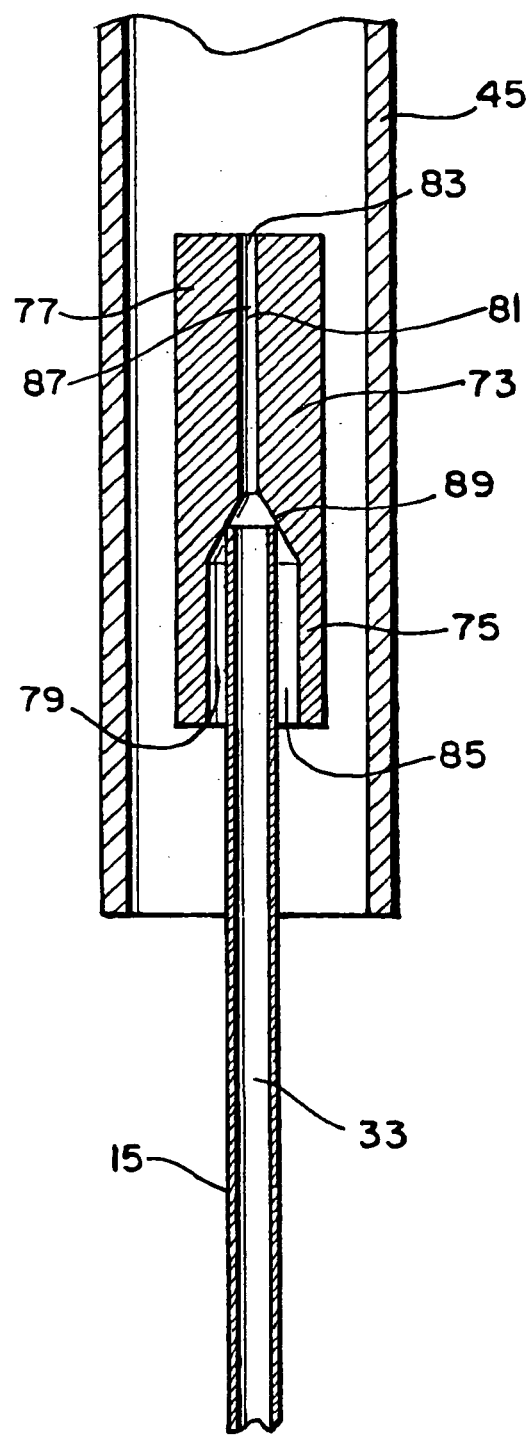
FIG. 6 is an enlarged view of a portion of the schematic view shown in FIG. 5.

Turning now to FIGS. 5 and 6, there is shown still another embodiment of our invention. In this embodiment of the invention, a gas chromatographic device 71 has a chromatography column 15, an inlet system 47 including a liner 45, and a column cap 73 as the pressure reducing means contained within the liner 45.

The column cap 73 has a ring-shaped wall 75 extending upright away from a top wall 77 and forming a chamber 79 therebetween. The top wall 77 has a passageway 81 extending therethrough to the chamber 79. The passageway 81 has an inlet portion 83 and an outlet portion 85, the outlet portion 85 leading to the chamber 79.

The passageway 81 has a pressure reducing portion 87 having a cross section sufficient to reduce the pressure of gas entering the passageway 81 through the inlet portion 83 of the passageway 81. Preferably, the passageway 81 has a diameter of 0.0001 to 5.0 mm, and a diameter between 0.015 mm and 0.030 mm is more preferred.

The column cap 73 also has a frusto-conical shaped surface 89 along the passageway 81 downstream of the pressure reducing portion 87 of the passageway 81 for contacting the inlet portion 29 of the chromatography column 15, thereby creating a gastight seal therebetween.

Preferably, the column cap 73 is made from an inert, substantially non-absorbing material such as glass, fused silica, quartz, chemically inert metal, inert material, or a material coated with an inert material, and may be manufactured by using glass drawing technology.

In use, the inlet portion 29 of the chromatography column 15 is placed within the liner 45 of the inlet system 47 of the gas chromatographic device 71, and the column cap 73 is placed on the inlet portion 29 of the chromatography column 15 such that the end portion of the chromatography column 15 at the inlet portion 29 of the chromatography column 15 is contained within the chamber 79 of the column cap 73 and the frusto-conical shaped surface 89 of the column cap 73 sits on the inlet portion 29 of the chromatography column 15 creating a gastight seal therebetween. Gas carrying the sample to be tested may be introduced to the liner 45, and then passed into the inlet portion 83 of the passageway 81 of the column cap 73 and through the passageway 81 to reduce the pressure of the gas, and then into and through the chromatography column 15.

If the column cap 73 becomes contaminated, it may be easily replaced by pulling it off the inlet portion 29 of the chromatography column 15 and placing a new column cap 73 in its place. Again, no tools or clipping are required to disconnect the column cap 73 from the chromatography column 15.

The pressure reducing means of the invention are designed for replacement without impacting the column/GC oven. Replacing one of the pressure reducing means of the invention for another essentially identical unit ensures high run-to-run performance consistency.

With our invention, the pressure reducing means is held at constant temperature, followed by temperature control in the oven for the column. This provides an advantage with respect to gas flow rates.

Because the inlet is held at constant temperature and the column is subjected to temperature control, our new devices 11, 41 and 71 may also be described as having a spatial element to the total temperature profile.

The invention claimed is:
1. A gas chromatographic device comprising
an inlet system, and
a chromatography column having an inlet portion,
the inlet system including a liner having pressure reducing means contained therein for reducing pressure between an inlet of the pressure reducing means and an outlet of the pressure reducing means, the liner having connection means for removably attaching the liner to the inlet portion of the chromatography column by merely stacking the liner onto the inlet portion of the chromatography column without creating a press-fit connection therebetween, and for detaching the liner from the inlet portion of the chromatography column by merely unstacking the liner from the inlet portion of the chromatography column without any need for tools and without any clipping of the chromatography column to disconnect the liner from the chromatography column, the pressure reducing means comprising a pressure reducing portion of a passageway extending through the liner, the pressure reducing portion of the passageway having a cross section smaller than that of the passageway upstream thereof, the pressure reducing portion of the passageway being hollow, the liner having a surface along the passageway downstream of the pressure reducing portion of the passageway which when the device is in use contacts the inlet portion of the chromatography column, the chromatography column when in use being positioned at its inlet in the liner downstream from the pressure reducing means, and the chromatography column when in use being under vacuum at its outlet.

2. The gas chromatographic device of claim 1, the pressure reducing portion of the passageway having a circular cross section having a diameter in a range between 0.0001 mm and 5.0 mm.

3. The gas chromatographic device of claim 1, the liner having a frusto-conical shaped surface along the passageway downstream of the pressure reducing portion of the passageway for contacting the inlet portion of the chromatography column and creating a gastight seal by contact between the frusto-conical shaped surface and the inlet portion of the chromatography column.

4. The gas chromatographic device of claim 3, the gastight seal consisting of the frusto-conical shaped surface of the liner contacting the inlet portion of the chromatography column.

5. The chromatographic device of claim 1, the pressure reducing portion of the passageway having a length of about 0.1 cm to about 2 cm.

6. The gas chromatopgraphic device of claim 1, wherein the pressure prevailing at said inlet of said pressure reducing means is in a range between 10 kPa and 1000 kPa, and pressure prevailing at said outlet of said chromatography column is substantially below an atmospheric pressure.

7. The gas chromatographic device of claim 1, wherein the pressure prevailing at an outlet of said pressure reducing means is in a range between 0.00001 kPa to 50 kPa.

8. The gas chromatographic device of claim 1, wherein said pressure reducing means comprises a pressure reducing portion of a passageway formed in a material selected from the group consisting of silica, glass, quartz, metal, an organic polymer, an inorganic polymer, and materials coated with an inert material.

9. The gas chromatographic device of claim 1, wherein said chromatography column is made from silica, glass, metal, an organic polymer, an inorganic polymer, or a combination thereof.

10. The gas chromatographic device of claim 1, wherein said pressure reducing means is formed by a capillary tube having a length in a range between 0.1 cm and 8 cm.

11. A gas chromatographic device comprising
an inlet system, and
a chromatography column,
the inlet system including a liner having pressure reducing means contained therein for reducing pressure between an inlet of the pressure reducing means and an outlet of the pressure reducing means,
the pressure reducing means comprising a pressure reducing portion of a passageway extending through the liner, the pressure reducing portion having a cross section smaller than that of the passageway upstream thereof,
the chromatography column when in use being positioned at its inlet in the liner downstream from the pressure reducing means, and
the chromatography column when in use being under vacuum at its outlet, the pressure reducing portion of the passageway being formed by a capillary tube secured to the liner, the capillary tube having a length of about 0.1 cm to about 2 cm.

12. A gas chromatographic device comprising
an inlet system, and
a chromatography column,
the inlet system including a liner having pressure reducing means contained therein for reducing pressure between an inlet of the pressure reducing means and an outlet of the pressure reducing means,
the chromatography column when in use being positioned at its inlet in the liner downstream from the pressure reducing means, and
the chromatography column when in use being under vacuum at its outlet,
the pressure reducing means being a capillary tube having an inlet portion and an outlet portion, and
the device further including
a column union for coupling the pressure reducing means to the chromatograph column,
the column union having a passageway extending therethrough between an inlet to the passageway and an outlet from the passageway, the union having an inverted frusto-conical shaped surface along the passageway of the column union for contacting the outlet portion of the capillary tube and creating a gastight seal therebetween, and the column union having an upright frusto-conical shaped surface along the passageway of the column union for contacting the inlet portion of the chromatography column and creating a gastight seal therebetween.

13. The chromatographic device of claim 12, the capillary tube having a diameter in a range between 0.005 mm to 5.0 mm.

14. The gas chromatographic device of claim 13, wherein said capillary tube is packed with particles, having an average size in a range between 0.5 μm and 500 μm.

15. The gas chromatographic device of claim 14, wherein said capillary tube is packed with deactivated particles.

16. The gas chromatographic device of claim 14, wherein said capillary tube is packed with non-deactivated particles.

17. The chromatographic device of claim 12, the capillary tube having a length of about 0.1 cm to about 8 cm.

18. The chromatographic device of claim 12, the capillary tube having a length of about 0.4 cm to about 2 cm.

19. The chromatographic device of claim 12, the column union having a length of about 2 cm.

20. A gas chromatographic device comprising
an inlet system, and
a chromatography column,
the inlet system including a liner having pressure reducing means contained therein for reducing pressure between an inlet of the pressure reducing means and an outlet of the pressure reducing means, the chromatography column when in use being positioned at its inlet in the liner downstream from the pressure reducing means, and the chromatography column when in use being under vacuum at its outlet, the pressure reducing means comprising a column cap, the column cap having a ring-shaped wall extending upright away from a top wall and forming a chamber therebetween, the top wall having a passageway extending therethrough to the chamber, the passageway having an inlet portion and an outlet portion, the outlet portion leading to the chamber, the passageway having a pressure reducing portion having a cross section sufficient to reduce the pressure of gas entering the passageway through the inlet portion of the passageway, the column cap having a frusto-conical shaped surface along the passageway downstream of the pressure reducing portion of the passageway for contacting an inlet portion of the chromatography column, thereby creating a gastight seal therebetween.

21. An inlet system of a gas chromatographic device, comprising a liner having pressure reducing means contained therein for reducing pressure between an inlet of the pressure reducing means and an outlet of the pressure reducing means, the pressure reducing means being a capillary tube having an inlet portion and an outlet portion, and the liner having a column union contained therein for coupling the pressure reducing means to a chromatography column, the column union having a passageway extending therethrough between an inlet to the passageway and an outlet from the passageway, the column union having first connection means for removably connecting the column union to an inlet portion of the chromatography column by merely stacking the column union onto the inlet portion of the chromatography column without creating a press-fit connection therebetween, and for detaching the column union from the inlet portion of the chromatography column by merely unstacking the column union from the inlet portion of the chromatography column without any need of tools and without clipping the chromatography column to disconnect the column union from the chromatography column, the column union having a second connection means for removably connecting the column union to the outlet portion of the capillary tube by merely stacking the capillary tube onto the column union without creating a press-fit connection therebetween, and for detaching the column union from the capillary tube by unstacking the capillary tube from the column union without any need for tools, the first connection means comprising an upright frusto-conical shaped surface along the passageway of the column union for contacting the inlet portion of the chromatography column and creating a gastight seal therebetween without creating a press-fit connection, and the second connection means comprising an inverted frusto-conical shaped surface along the passageway for contacting the outlet portion of the capillary tube and creating a gastight seal therebetween without creating a press-fit connection.

22. An inlet system of a gas chromatographic device, comprising a liner having pressure reducing means contained therein for reducing pressure between an inlet of the pressure reducing means and an outlet of the pressure reducing means, the pressure reducing means comprising a column cap, the column cap having a ring-shaped wall extending upright away from a top wall and forming a chamber therebetween, the top wall having a passageway extending therethrough to the chamber, the passageway having an inlet portion and an outlet portion, the outlet portion leading to the chamber, the passageway having a pressure reducing portion having a cross section sufficient to reduce the pressure of gas entering the passageway through the inlet portion of the passageway, the column cap having a frusto-conical shaped surface along the passageway downstream of the pressure reducing portion of the passageway for contacting an inlet portion of a chromatography column and creating a gastight seal therebetween.

* * * * *